United States Patent [19]

Yahagi et al.

[11] Patent Number: 5,714,136
[45] Date of Patent: Feb. 3, 1998

[54] HAIR COSMETIC CONTAINING A CATIONIC SURFACTANT, FAT AND OIL AND AN ALKYL SACCHARIDE SURFACTANT

[75] Inventors: Kazuyuki Yahagi, Tokyo; Kazuhiro Tashiro, Kanagawa; Takashi Koyama; Yoshiyuki Eshita, both of Chiba; Tsuyoshi Ohtomo; Fumiko Sazanami, both of Saitama; Jun Kamegai, Chiba, all of Japan

[73] Assignee: Kao Corporation, Tokyo, Japan

[21] Appl. No.: 384,802

[22] Filed: Feb. 6, 1995

Related U.S. Application Data

[63] Continuation of Ser. No. 208,188, Mar. 10, 1994, abandoned, which is a continuation of Ser. No. 962,921, Oct. 19, 1992, abandoned.

[30] Foreign Application Priority Data

Oct. 22, 1991 [JP] Japan ................................ 3-274007
Feb. 12, 1992 [JP] Japan ................................ 4-025357

[51] Int. Cl.⁶ .............................. A61K 7/07; A61K 7/08
[52] U.S. Cl. .............................. 424/70.19; 424/70.28; 424/70.31; 424/70.12; 424/70.122
[58] Field of Search ........................ 424/70.19, 70.28, 424/70.31, 70.12, 70.1, 70.122

[56] References Cited

U.S. PATENT DOCUMENTS

| | | | |
|---|---|---|---|
| 3,219,656 | 11/1965 | Boettner | 536/18.6 |
| 3,850,833 | 11/1974 | Koceich | 252/99 |
| 4,223,129 | 9/1980 | Roth | 536/18.6 |
| 4,323,559 | 4/1982 | Bernhard | 424/69 |
| 4,798,721 | 1/1989 | Yahagi et al. | 424/70 |
| 4,919,846 | 4/1990 | Nakama et al. | |
| 5,013,486 | 5/1991 | Joshi | 252/559 |
| 5,051,251 | 9/1991 | Morita | 514/772 |
| 5,057,311 | 10/1991 | Kamegai | 424/70 |
| 5,077,039 | 12/1991 | Baur | 424/70 |

FOREIGN PATENT DOCUMENTS

| | | |
|---|---|---|
| 0 106 692 A1 | 10/1983 | European Pat. Off. |
| 0 268 992 A2 | 11/1987 | European Pat. Off. |
| 0 422 508 A2 | 10/1990 | European Pat. Off. |
| 2 128 627 | 9/1983 | United Kingdom |
| WO 86/05509 | 9/1986 | WIPO |
| WO 92/06778 | 4/1992 | WIPO |

OTHER PUBLICATIONS

*Patent Abstracts of Japan*, vol. 16, No. 054 (C–909) 12 Feb. 1992 & JP-A-32 55 019 (Lion Corp.) 13 Nov. 1991.

*Primary Examiner*—Sally Gardner-Lane
*Attorney, Agent, or Firm*—Oblon, Spivak, McClelland, Maier & Neustadt, P.C.

[57] ABSTRACT

A hair cosmetic is disclosed which comprises the following components (A), (B) and (C):

(A) a cationic surfactant;
(B) a fat and/or an oil; and
(C) an alkyl saccharide surfactant represented by the following formula (1):

$$R^1-O-(R^2O)_m-G_n \quad (1)$$

wherein the weight ratio of (A)/(C) is from 1 to 20. A hair cosmetic which further comprises fine particles of an average particle size of 100 μm or below as the component (D) is also disclosed. The hair cosmetic of the present invention gives a good smoothness, a good elasticity and an oil-free feel to the hair without imparting any sticky feel or dry and loose feel thereto.

10 Claims, No Drawings

HAIR COSMETIC CONTAINING A CATIONIC SURFACTANT, FAT AND OIL AND AN ALKYL SACCHARIDE SURFACTANT

This application is a Continuation of application Ser. No. 08/208,188, filed on Mar. 10, 1994, which was a Continuation of application Ser. No. 07/962,921, filed on Oct. 19, 1992, both now abandoned.

FIELD OF THE INVENTION

This invention relates to a hair cosmetic (for example, hair rinse, hair conditioner, hair treatment, hair cream) which can give a good smoothness, a good tension and resilience (elasticity) and an oil-free feel to the hair without imparting any sticky feel or dry and loose feel thereto.

BACKGROUND OF THE INVENTION

In order to improve the texture of the hair, conventional hair cosmetics contain various cationic surfactants such as mono- or di-straight long chain alkyl quaternary ammonium salts and mono- or di-branched long chain alkyl quaternary ammonium salts. In recent years, it is attempted to use these cationic surfactants together with fats and oils such as higher alcohols, glyceride, liquid paraffin and ester oils in order to impart a good smoothness and a high moistness to the hair.

However, these hair cosmetics still show only insufficient smoothness and moistness at the finishing. When the contents of oily components are elevated so as to improve the smoothness and moistness, however, the hair becomes oily and sticky and no oil-free feel can be obtained. Further, these hair cosmetics are disadvantageous in that, when they are applied to a hair which is soft and poor in elasticity, they make the hair less voluminous and, therefore, a good hair style cannot be formed.

On the other hand, JP-A-64-38015 discloses a hair rinse composition which contains a specific amphoteric surfactant and a cationic polymer in order to improve the resilience of the hair (the term "JP-A" as used herein means an "unexamined published Japanese Patent Application"). Although the addition of such a polymer can improve the resilience of the hair, no oil-free feel can be obtained thereby.

Thus, it is an object of the present invention to provide a hair cosmetic which can give a smoothness, a good elasticity and an oil-free feel to the hair without imparting any sticky feel or dry feel thereto.

SUMMARY OF THE INVENTION

In the circumstances, the present inventors have conducted extensive investigations, and found that by adding an alkyl saccharide surfactant represented by the following formula (1) in a specific amount, a hair cosmetic capable of giving a good smoothness, a good elasticity and an oil-free feel to the hair without imparting any sticky feel or dry and loose feel thereto can be obtained. This completed the present invention.

Accordingly, the present invention provides a hair cosmetic comprising the following components (A), (B) and (C):

(A) a cationic surfactant;
(B) a fat and an oil; and
(C) an alkyl saccharide surfactant represented by the following formula (1):

$$R^1\text{—}O\text{—}(R^2O)_m\text{—}G_n \qquad (1)$$

wherein
$R^1$ represents a straight chain or branched chain alkyl, alkenyl or alkylphenyl group having 8 to carbon atoms;
$R^2$ represents an alkylene group having 2 to 4 carbon atoms;
m represents a number of 0 to 10;
G represents a reducing sugar having 5 or 6 carbon atoms; and
n represents a number of 1 to 10, wherein the weight ratio of the component (A) to the component (C) is from 1 to 20.

DETAILED DESCRIPTION OF THE INVENTION

Examples of the cationic surfactant of the component (A) to be used in the present invention include, for example, quaternary ammonium salts represented by the following formula (2) or (3):

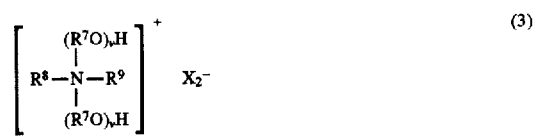

wherein
at least one of $R^3$, $R^4$, $R^5$ and $R^6$ represents an alkyl or alkenyl group having 8 to 28 carbon atoms in total and optionally substituted with an alkoxyl, alkenyloxy, alkanoyl-amino or alkenoylamino group, while the others represent each a benzyl group or an alkyl or hydroxyalkyl group having 1 to carbon atoms;
$R^7$ represents an alkylene group having 2 or 3 carbon atoms;
$X_1^-$ and $X_2^-$ represent each a halogen ion or an organic anion;
v and v' represent each an integer of from 1 to 20; and
at least one of $R^8$ and $R^9$ represents an alkyl or alkenyl group having 8 to 28 carbon atoms in total and optionally substituted with an alkoxyl, alkenyloxy, alkanoylamino or alkenoylamino group while the other represents a benzyl group or an alkyl or hydroxyalkyl group having 1 to 5 carbon atoms.

Among these cationic surfactants, quaternary ammonium salts represented by the above formula (2) are preferred. Examples of more preferred ones include branched quaternary ammonium salts represented by the following formulae (4) to (6).

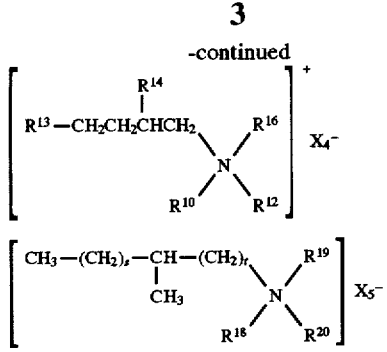

wherein
$R^{10}$ represents a mixture of:
(a) a branched alkyl group represented by formula

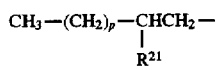

(wherein $R^{21}$ is a methyl or ethyl group; and p represents an integer giving the total carbon atom number in the alkyl group of 8 to 16); and (b) a straight-chain alkyl group represented by formula $CH_3$—$(CH_2)_q$— (wherein q is an integer of 7 to 15), wherein the branching ratio defined by (a)/((a)+(b)) is from 10 to 100% by mol;

$R^{11}$ and $R^{12}$ represent each a benzyl group or an alkyl or hydroxyalkyl group having 1 to 3 carbon atoms;

$R^{13}$ and $R^{14}$ represent each an alkyl group having 2 to 12 carbon atoms;

$R^{15}$ represents a group represented by formula

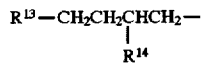

or an alkyl group having 1 to 3 carbon atoms;

$R^{16}$ and $R^{17}$ represent each a benzyl group or an alkyl or hydroxyalkyl group having 1 to 3 carbon atoms;

$R^{18}$ represents a group represented by formula

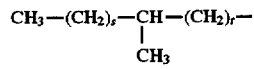

(wherein s represents an integer of 2 to 14 and t represents an integer of 3 to 11, provided that the sum of s and t is from 9 to 21) or an alkyl group having 1 to 3 carbon atoms;

$R^{19}$ and $R^{20}$ represent each a benzyl group or an alkyl or hydroxyalkyl group having 1 to 3 carbon atoms; and $X_3^-$, $X_4^-$ and $X_5^-$ represent each a halogen ion or an organic anion.

The branched quaternary ammonium salt represented by the above formula (4) may conventionally be synthesized by using, for example, an oxoalcohol having 8 to 16 carbon atoms. Examples thereof include dialkyldimethylammonium salts, dialkylmethylhydroxyethylammonium salts and dialkylmethylbenzylammonium salts each having an alkyl group derived from oxoalcohols.

In the present invention, the branching ratio of $R^{10}$ in formula (4) generally ranges from 10 to 100% by mol, preferably from 10 to 50% by mol. Further, $R^{10}$ of a total carbon atom number of from 8 to 16 may preferably be used. It is preferable that the carbon atom number distribution falls within a definite range. Now a particularly preferable example of the distribution will be shown below:

$C_8$–$C_{11}$: 5% by mol or below,
$C_{12}$: 10–35% by mol,
$C_{13}$: 15–40% by mol,
$C_{14}$: 20–45% by mol,
$C_{15}$: 5–30% by mol, and
$C_{16}$: 5% by mol or below.

Particular examples of such a branched quaternary ammonium salt (4) include dialkyldimethylammonium chlorides having an alkyl group of 8 to 16 carbon atoms and of a branching ratio of 10 to 50% by mol.

The branched quaternary ammonium salt represented by the above formula (5) may conventionally be synthesized by using a Guerbet alcohol having 8 to 28 carbon atoms and represented by the following formula:

wherein $R^{13}$ and $R^{14}$ are as defined above.

Preferred examples of the branched quaternary ammonium salt of this type include alkyltrimethylammonium salts, alkyldimethylbenzylammonium salts, dialkyldimethylammonium salts, dialkylmethylhydroxyethylammonium salts and dialkylmethylbenzylammonium salts having an alkyl group derived from Guerbet alcohols. Among these quaternary ammonium salts, 2-decyltetradecyltrimethylammonium chloride, 2-dodecylhexadecyltrimethylammonium chloride, di-2-hexyldecyldimethylammonium chloride and di-2-octyldodecyl-dimethylammonium chloride are particularly preferred.

Preferred examples of the methyl branched quaternary ammonium salt represented by the above formula (6) include those wherein the sum of s and t is 15.

Specific examples of the counter ions ($X_1^-$ to $X_5^-$) in the quaternary ammonium salts represented by the above formulae (2), (3), (4), (5) and (6) include halogen ions such as chlorine, iodine and bromine ions; and organic anions such as methosulfate, ethosulfate, methophosphate and ethophosphate.

As the cationic surfactant of the component (A), either one of these compounds or a mixture thereof may be employed. The content thereof in the hair cosmetic of the present invention amounts from 0.1 to 20% by weight, preferably from 0.5 to 15% by weight, based on the total composition. When the content of the component (A) is smaller than 0.1% by weight, the effects of the present invention lower. On the other hand, it is undesirable that its content exceeds 20.0% by weight, since a sticky feel tends to be imparted to the hair in this case.

The fat and oil to be used as the component (B) in the present invention may be selected from among those commonly employed in hair cosmetics, without restriction. For example, higher alcohols having straight chain or branched alkyl or alkenyl groups; hydrocarbons such as liquid paraffin, vaseline and solid paraffin; lanolin derivatives such as liquid lanolin and lanolin fatty acids; higher fatty acid esters; higher fatty acids and long chain amide amines having alkyl or alkenyl groups; and vegetable and animal fats and oils such as mink oil and olive oil may be used therefor. Among these fats and oils, monoglycerides originating from saturated or unsaturated, straight chain or branched fatty acids having 12 to 24 carbon atoms, and higher alcohols having straight chain or branched alkyl or alkenyl group(s) having 12 to 26 carbon atoms are particularly preferred. Specific examples thereof include fatty acid monoglycerides such as oleic acid monoglyceride, palmitic acid monoglyceride, behenic acid monoglyceride and isostearic acid monoglyceride and higher alcohols such as cetyl alcohol, stearyl alcohol, arachic alcohol, behenyl alcohol and ceryl alcohol.

Either one of these fats and oils or a mixture thereof may be used. The content thereof in the hair cosmetic of the present invention amounts from 0.2 to 30% by weight, preferably from 0.5 to 20% by weight, based on the total composition. When the content of the component (B) is smaller than 0.2% by weight, the effects of the present invention lower. On the other hand, it is undesirable that its content exceeds 30% by weight, since a sticky feel is sometimes imparted to the hair in this case.

The alkyl saccharide surfactant of the component (C) is represented by the above formula (1). Among these compounds, those wherein $R^1$ is an alkyl group having 8 to 18, more preferably 8 to 12, carbon atoms (for example, octyl group, decyl group, lauryl group) are particularly preferable. m, which represents the degree of polymerization of the alkylene oxide, is a number of from 0 to 10. It is preferable that m is from 0 to 4, more preferably 0. As the reducing sugar represented by G, glucose, galactose and fructose are preferred. The average degree of polymerization of the saccharide represented by n ranges from 1 to 10, preferably from 1 to 4. It is desirable that the average degree of polymerization represented by n is selected by taking the properties originating from the hydrophobic group $R^1$ into consideration. When $R^1$ is a hydrophobic group having from 8 to 11 carbon atoms on average, for example, n preferably ranges from 1 to 1.4. When $R^1$ is a hydrophobic group having from 12 to 14 carbon atoms on average, on the other hand, it is preferable that n ranges from 1.5 to 4.0. The average polymerization degree of the sugar(s) many be determined by the proton NMR.

The content of the component (C) is determined based on the weight ratio to the component (A). Namely, the weight ratio of the component (A) to the component (C) ((A)/(C)) may range from 1 to 20, preferably from 2 to 10. When this weight ratio exceeds 20, the hair tends to become sticky and no good elasticity can be imparted to the hair. When it is less than 1, on the other hand, the hair may become poor in softness and slipping properties in a wet state.

The hair cosmetic of the present invention may further contain fine particles of an average particle size of 100 μm or below as the component (D). The lower limit of the average particle size of the fine particles is preferably 0.005 μm.

The fine particles to be used in the present invention are not particularly restricted, so long as they are hardly soluble in water but dispersible therein. For example, organic polymers, silicone resins, clay minerals or organic polyvalent metal salts may be used therefor.

Examples of the organic polymers include nylon, polyethylene, polyester, polypropylene, polystyrene, polyurethane, polyamide, epoxy resins, urea resins and acryl polymers. Further, copolymers and crosslinked products thereof are also usable therefor. In general, among these materials, it is preferable to use a polymer latex synthesized via emulsion polymerization, for example, an organic polymer latex of an average particle size of from 0.005 to 0.2 μm, wherein at least 95% by weight, based on the whole, of the particles fall within a particle size range of 0.005 to 0.2 μm, which is disclosed in JP-A-62-63508 (corresponding to EP-A-214626).

Examples of the silicone resins include one disclosed, for example, in JP-A-165509. A specific example thereof includes one available from Toshiba Silicone Co., Ltd. under tradename Tospearl.

Examples of the clay minerals include talc, kaolin, mica, sericite and bentonite.

Examples of the organic polyvalent metal salts include 2-mercaptopyridine polyvalent metal salts and selenium disulfide, preferably, 2-mercaptopyridine zinc salt (zinc pyrithione). As 2-mercaptopyridine zinc salt, it is particularly preferable to use fine particles of which particles of 0.2 μm or below amount 50% by weight or more and having an average particle size of 0.2 μm or below, as disclosed in JP-A-60-16972, JP-A-60-16973 and JP-A-60-224676 (corresponding to EP-A-133914).

Among these fine particles, the silicone resins and the organic polyvalent metal salts are preferred and the latter ones are more preferred.

The content of the component (D) is determined based on the weight ratio to the component (A). Namely, the weight ratio of the component (A) to the component (D) ((A)/(D)) may range from 1 to 20, preferably from 2 to 10. When this weight ratio exceeds 20, the hair tends to become sticky and any oil-free feel or any good elasticity hard to be imparted to the hair. When it is less than 1, on the other hand, the hair may become poor in smoothness. It is described above that the average particle size of these fine particles is 100 μm or below. It is preferable that the average particle size is 20 μm or below. When the average particle size exceeds 100 μm, the hair may show a poor smoothness and, further, the stability of the system may be worsened and, as a result, it is feared that the system might separate out.

The hair cosmetic of the present invention may further contain a silicone derivative as the component (E) in order to improve the texture. Examples of the silicone derivative are as follows.

(a) Dimethylpolysiloxanes represented by the following formula (7):

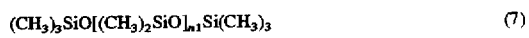

wherein n1 is an integer of 3 or above.

An example of the dimethylpolysiloxanes represented by the above formula (7) include that marketed under tradename KF96 from Shin-Etsu Chemical Co., Ltd. In the present invention, dimethylpolysiloxanes having a viscosity of 1 to 20,000,000 cs are useful.

(b) Methylphenylpolysiloxanes represented by the following formula (8):

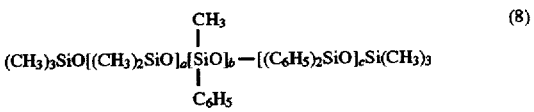

wherein a, b and c are numbers the sum of which exceeds 1, provided that c is not 0 when b is 0 and b is not 0 when c is 0, and further provided that the sum of a, b and c is 20,000 or less.

The methylphenylpolysiloxanes represented by the above formula (8) are widely known. For example, one marketed by Shin-Etsu Chemical Co., Ltd. under tradename of KF150 may be used therefor. In the present invention, methylphenylpolysiloxanes having a viscosity of 100 to 20,000,000 cs are useful.

(c) Amino-modified silicones represented by the following formula (9):

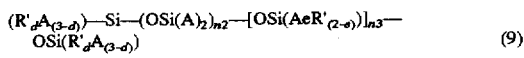

wherein
- A represents a hydrogen atom or a group selected from among a phenyl group, a hydroxyl group and an alkyl group having 1 to 8 carbon atoms;
- d is an integer of from 0 to 3;
- e is 0 or 1;
- n2 is an integer of from 0 to 1,999;
- n3 is an integer of from 1 to 2,000, provided that the sum of n2 and n3 is an integer of from 1 to 2,000; and
- R' is a group —$C_fH_{2f}$L (wherein f is an integer of from 2 to 8; and L is selected from among:

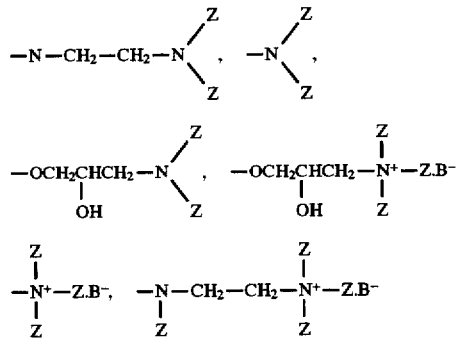

(wherein Z represents a hydrogen atom or a group selected from among a phenyl group, a benzyl group and an alkyl group having 1 to 20 carbon atoms; and $B^-$ represents $Cl^-$, $Br^-$, $I^-$ or $F^-$)).

Examples of the amino-modified silicones represented by the above formula (9) include SF8417, DC536 and aminoalkylsilicone emulsion SM8702, tradenames, each manufactured by Toray Dow Corning Silicone Co.

(d) Fatty acid-modified polysiloxanes represented by the following formula (10):

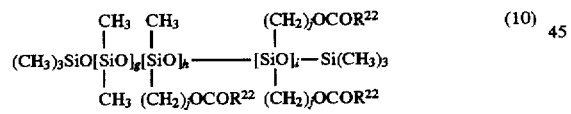

wherein
- g, h and i are each a number of from 1 to 350;
- j is a number of from 0 to 10; and
- $R^{22}$ represents an alkyl group having 9 to 21 carbon atoms.

An example thereof includes one available from Shin-Etsu Chemical Co., Ltd. under trademark KF-910 (m.p. 45° C.).

(e) Alcohol-modified silicones represented by the following formula (11-a) or (11-b):

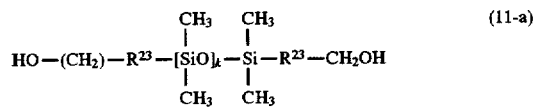

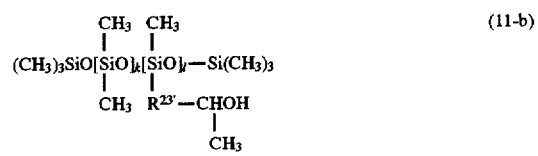

wherein
- k is a number of from 1 to 500, preferably from 1 to 200; and
- $R^{23}$ and $R^{23'}$ represent each a single bond or an alkylene group having 1 to 4 carbon atoms.

An example thereof includes one available from Toray Dow Corning Co., Ltd. under tradename BY16-848 (55 cs).

(f) Aliphatic alcohol-modified silicones represented by the following formula (12):

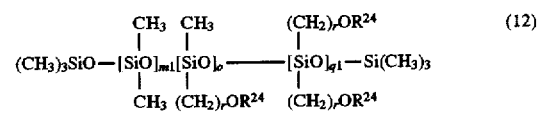

wherein
- m1, o and q1 are each a number the sum of which is from 1 to 300;
- r is a number of from 0 to 5; and
- $R^{24}$ represents an alkyl group having 4 to 22 carbon atoms.

More specific examples thereof include ones wherein $R^{24}$ is $C_{18}H_{37}$, m1 is 5 to 30, r is 0, o is 2 to 15, and q1 is 0.

(g) Polyether-modified silicones represented by the following formulae (13) to (16):

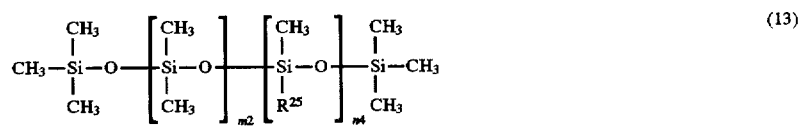

$$R^{25}-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_{m2}\left[\underset{\underset{R^{25}}{|}}{\overset{\overset{CH_3}{|}}{Si}}-O\right]_{n4}\underset{\underset{CH_3}{|}}{\overset{\overset{CH_3}{|}}{Si}}-R^{25} \quad (15)$$

$$CH_3-\underset{\underset{CH_3}{|}}{\overset{\overset{CH_3}{|}}{Si}}-O-\left[\left[\underset{\underset{CH_3}{|}}{\overset{\overset{CH_3}{|}}{Si}}-O\right]+CH_2\!\!\!\!-_{z1}\!\!-O+C_2H_4O\!\!\!\!-_{x1}\!(C_3H_6O\!\!\!\!-_{y1}\!(CH_2\!\!\!\!-_{z1}\right]_{m2}-\underset{\underset{CH_3}{|}}{\overset{\overset{CH_3}{|}}{Si}}-CH_3 \quad (16)$$

wherein $R^{25}$ represents a group $-(CH_2)_{z1}-O-(C_2H_4O)_{x1}-(C_3H_6O)_{y1}-A_1$ (wherein $A_1$ represents an alkyl group having 1 to 12 carbon atoms or a hydrogen atom; x1 is a number of from 0 to 50; y1 is a number of from 0 to 50, provided that the sum of x1 and y1 is 1 or above; z1 is a number of from 0 to 10; m2 is a number of from 1 to 2,000; and n4 is a number of from 1 to 1,000).

More specific examples of the compound represented by formula (13) include ones wherein $R^{25}$ is $C_3H_6O-(C_2H_4O)_{5-20}$, m2 is 5 to 50 and n4 is 1 to 10.

Examples of the compound represented by formula (16) include ones available from Shin-Etsu Chemical Co., Ltd. under tradenames of KF351A and KF6005.

(h) Epoxy-modified silicones represented by the following formula (17):

$$(CH_3)_3SiO[\underset{\underset{CH_3}{|}}{\overset{\overset{CH_3}{|}}{Si}O}]_\alpha[\underset{\underset{R^{26}-CH-CH_2}{|}\underset{\diagdown\ O\ \diagup}{}}{\overset{\overset{CH_3}{|}}{Si}O}]_\beta-Si(CH_3)_3 \quad (17)$$

wherein

α is a number of from 1 to 500, preferably from 1 to 250;

β is a number of from 1 to 50, preferably from 1 to 30; and $R^{26}$ is an alkylene group having 1 to 3 carbon atoms.

An example thereof include one available from Shin-Etsu Chemical Co., Ltd. under tradename KF-103.

(i) Fluorine-modified silicones represented by the following formula (18):

$$(CH_3)_3SiO(\underset{\underset{\underset{CF_3}{|}}{\underset{(CH_2)_2}{|}}}{\overset{\overset{CH_3}{|}}{Si}O})_\gamma-Si(CH_3)_3 \quad (18)$$

wherein γ is a number of from 1 to 400, preferably from 1 to 250.

An example thereof includes one available from Toray Dow Corning Co., Ltd. under tradename FS1265 (1,000 cs).

(j) Cyclic silicones represented by the following formula (19):

$$\left[\!\!\begin{array}{c}R^{27}\\|\\ SiO\\|\\R^{27}\end{array}\!\!\right]_\delta \quad (19)$$

wherein

δ is a number of from 3 to 8; and

R27 represents an alkyl group having 1 to 3 carbon atoms.

More specific examples thereof include ones wherein $R^{27}$ is $CH_3$ and δ is 3 to 5 (e.g., octamethylcyclotetrasiloxane, decamethyl-cyclopentasiloxane).

(k) Alkyl-modified silicones represented by the following formula (20-a) or (20-b):

$$(CH_3)_3SiO[\underset{\underset{R^{28}}{|}}{\overset{\overset{CH_3}{|}}{SiO}}]_\epsilon[\underset{\underset{R^{29}}{|}\underset{\bigcirc}{}}{\overset{\overset{CH_3}{|}}{SiO}}]_\zeta-Si(CH_3)_3 \quad (20\text{-a})$$

$$(CH_3)_3SiO[\underset{\underset{CH_3}{|}}{\overset{\overset{CH_3}{|}}{SiO}}]_\epsilon[\underset{\underset{R^{30}}{|}}{\overset{\overset{CH_3}{|}}{SiO}}]_\zeta-Si(CH_3)_3 \quad (20\text{-b})$$

wherein

ε and ζ are each a number of from 1 to 500, preferably from 1 to 200;

$R^{28}$ represents an alkyl group having 2 to 18 carbon atoms;

$R^{29}$ represents a single bond or an alkylene group having 1 to 4 carbon atoms; and $R^{30}$ represents an alkyl group having 10 to 16 carbon atoms.

More specific examples of the compounds represented by formula (20-a) include ones wherein $$R^{29}-\bigcirc \text{ is } -CH_2-\underset{\underset{CH_3}{|}}{CH}-\bigcirc$$

(ones having viscosity of 1,000 cs).

An example of the compound represented by formula (20-b) include one available from Shin-Etsu Chemical Co., Ltd. under tradename KF413 (100 cs).

Each of these silicone derivatives makes it possible to fully exert the effects of the present invention. From the viewpoint of improving the smoothness and the elasticity of the hair, it is recommended to use dimethylpolysiloxanes (a), amino-modified silicones (c), polyether-modified silicones (g) and cyclic silicones (j).

In the dimethylpolysiloxanes (a), n1 in the formula (7) may be selected from a range of 3 to 9,000 depending on the desired finishing feel. In order to give a sufficient elasticity to the hair, it is preferable that n1 is at least 1,000, more preferably from 2,000 to 7,000. As the amino-modified silicones (c), preferred examples thereof include ones represented by the formula (9) wherein d is 0, e is 1, f is 3, A is a hydroxyl group and a methyl group and L is $-NHCH_2CH_2NH_2$, which is called as amodimethycone in U.S.A. Encyclopedia of CTFA. The amodimethycone can be represented by the following formula (9'):

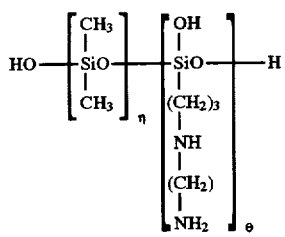

(9')

wherein

η and θ represent each a number to give a molecular weight of from 3,000 to 100,000.

In the present invention, either one of these silicone derivatives or a combination thereof may be used as the component (E). The content of these silicone derivatives in the hair cosmetic composition may usually range from 0.05 to 20% by weight, more preferably from 0.1 to 10% by weight.

If required, the other components, which are commonly used in cosmetics, drugs and foods, may be added to the hair cosmetic of the present invention in amounts which do not impair the effects of the present invention. Examples of these additives include medical components such as anti-dandruff agents (for example, octopirox), bactericides and vitamins; preservatives such as paraben; humectants such as propylene glycol, glycerol, diethylene glycol monoethyl ether, sorbitol, pantenol and glycine betaine; thickeners such as water-soluble polymers; colorants such as dyes and pigments; conditioning agents such as perfluoropolyether and cationic polymers; pearling agents such as glycol esters; hair-setting polymers such as chitosan derivatives (for example, hydroxypropylchitosan) and acryl resin solutions; various perfume preparations; and those listed in Encyclopedia of Conditioning Rinse Ingredients (Micelle Press, 1987).

The hair cosmetic of the present invention is produced in a conventional manner by using the above-mentioned components. It may be suitably formulated into hair cosmetics which are to be applied to the hair, following shampooing, and then washed away (for example, hair rinse, hair conditioner, hair treatment).

The hair cosmetic of the present invention may be produced by mixing the above-mentioned components in a conventional manner.

The hair cosmetic of the present invention can give a high smoothness, a good elasticity and an oil-free feel to the hair without showing any sticky or dry and loose feel. Thus it is particularly suitable for soft hair poor in elasticity.

To further illustrate the present invention in greater detail, and not by way of limitation, the following Examples will be given.

EXAMPLES 1 AND 2

Hair rinses of the compositions as listed in Table 1 were produced by the following method and the performance of each product was evaluated by an organoleptic test as specified below. Table 1 summarizes the results. Organoleptic evaluation method:

20 g of fine hairs (average diameter: 60 μm; length: 15 cm) of a Japanese female subject, which had never been cold-permed nor bleached, was bundled. In the case of a hair cosmetic to be washed away, 2 g of the hair cosmetic was uniformly applied to the hair bundle and then washed away with running water for 30 seconds. After towel-drying, the hair was dried with a dryer. In the case of a hair cosmetic not to be washed away, on the other hand, a definite amount of the hair cosmetic was applied to the hair bundle, followed by air-drying. Then the less sticky feel, less dry/loose feel, smoothness and elasticity of each hair bundle were organoleptically evaluated. A means "very good", B means "good", C means "moderate" and D means "poor".

Production method:

To the component (7) heated to 70° C., a mixture of the components (1) to (6), which had been molten by heating to the same temperature, was added. After emulsifying by stirring, the emulsion was cooled to room temperature under stirring to thereby give a hair rinse product.

TABLE 1

|   |   | Example 1 | Example 2 | Comparative Example 1 | Comparative Example 2 |
|---|---|---|---|---|---|
| (1) | Stearyltrimethyl-ammonium chloride | 1 | 0.7 | 1 | 0.7 |
| (2) | Distearyldimethyl-ammonium chloride | — | 0.3 | — | 0.3 |
| (3) | Cetostearyl alcohol | 4 | 3 | 4 | 3 |
| (4) | Alkyl saccharide ($C_{12}$-O-(G)$_{2.0}$) | 0.4 | 0.2 | — | — |
| (5) | Lanolin | — | 2 | — | 2 |
| (6) | Propylene glycol | 3 | 3 | 3 | 3 |
| (7) | Water | balance | balance | balance | balance |
|   | Ratio (A) / (C) (by weight) | 2.5 | 5 | — | — |
|   | Effects: |   |   |   |   |
|   | Less sticky feel | A | B | C | D |
|   | Less dry/loose feel | B | A | B | B |
|   | Smoothness | B | B | C | D |
|   | Elasticity | A | A | D | D |

EXAMPLE 3

Hair conditioner products of Example 3 and Comparative Example 3 of the following compositions were produced by the methods as specified below.

The performances of these products were evaluated by a pair comparison test with the use of 16 female panelists. In this test, +2 means "very good", +1 means "good" and 0 means "equivocal" and the results are expressed in the number of panelists. Table 2 summarizes the results.

Composition of Hair Conditioner of Example 3

| Component | Amount (% by weight) |
|---|---|
| (1) Cetostearyltrimethylammonium chloride | 1.0 |
| (2) Dicetyldimethylammonium chloride | 0.5 |
| (3) Cetanol | 4 |
| (4) Alkyl saccharide ($C_{12}$-O-(G)$_{1.7}$) | 0.5 |
| (5) Propylene glycol | 5 |
| (6) Perfume | 0.4 |
| (7) Water | balance |
| Ratio (A) / (C) (by weight): | 3 |

Production method:

To the component (7) heated to 70° C., a mixture of the components (1) to (5), which had been molten by heating to the same temperature, was added. After emulsifying by stirring, the obtained emulsion was cooled to 40° C. under stirring. Then the component (6) was added thereto and the mixture was further cooled to room temperature under stirring to thereby give a hair conditioner product.

Composition of Hair Conditioner of Comparative Example 3

| Component | Amount (% by weight) |
|---|---|
| (1) Cetostearyltrimethylammonium chloride | 1 |
| (2) Dicetyldimethylammonium chloride | 0.5 |
| (3) Cetanol | 4 |
| (4) Propylene glycol | 5 |
| (5) Perfume | 0.4 |
| (6) Water | balance |

Production method:

To the component (6) heated to 70° C., a mixture of the components (1) to (4), which had been molten by heating to the same temperature, was added. After emulsifying by stirring, the obtained emulsion was cooled to 40° C. under stirring. Then the component (5) was added thereto and the mixture was further cooled to room temperature under stirring to thereby give a hair conditioner product.

TABLE 2

| | Example 3 | | | Comparative Example 3 | |
|---|---|---|---|---|---|
| | +2 | +1 | 0 | +1 | +2 |
| Total evaluation | 1 | 4 | 8 | 3 | 0 |
| Less sticky finishing | 2 | 6 | 6 | 2 | 0 |
| Less dry finishing | 0 | 3 | 11 | 2 | 0 |
| Smooth finishing | 1 | 6 | 5 | 3 | 1 |
| Elastic finishing | 2 | 4 | 8 | 2 | 0 |

EXAMPLES 4 TO 7

Hair cosmetics of the compositions specified in Tables 3 and 4 were produced by the following method and the rinse performances of these products were evaluated in accordance with the evaluation method employed in the above Examples 1 and 2. Tables 3 and 4 show the results.

Production method:

To a mixture of the components (6) and (7) heated to 70° C., a mixture of the components (1) to (5), which had been molten by heating to the same temperature, was added. After emulsifying by stirring, the obtained emulsion was cooled to room temperature under stirring.

TABLE 3

| | | Example | | | |
|---|---|---|---|---|---|
| | | 4 | 5 | 6 | 7 |
| (1) | Stearyltrimethylammonium chloride | 1.2 | — | 0.8 | 0.4 |
| | Behenyltrimethylammonium chloride | — | 1.0 | — | 0.2 |
| | 2-Hexyldodecyltrimethylammonium chloride | 0.6 | — | — | 0.2 |
| | Di-2-hexyldecyldimethylammonium chloride | — | 0.8 | 0.2 | — |
| (2) | Cetostearyl alcohol | 6.0 | 6.0 | 3.0 | 2.5 |
| (3) | Alkyl saccharide | | | | |
| | $C_{10}$-O-$(G)_{1.5}$ | 0.2 | — | — | — |
| | $C_{12}$-O-$(G)_{2.0}$ | — | 0.1 | — | 0.3 |
| | $C_{12}$-$(EO)_2$-G | — | — | 0.3 | — |

TABLE 3-continued

| | | Example | | | |
|---|---|---|---|---|---|
| | | 4 | 5 | 6 | 7 |
| (4) | Dimethylpolysiloxane (1,000 cs) | 0.1 | — | — | — |
| | Dimethylpolysiloxane (20,000,000 cs) | — | 0.5 | — | — |
| | Amino-modified silicone*1 | — | — | 1.0 | — |
| | Polyether-modified silicone*2 | — | — | — | 0.5 |
| (5) | Propylene glycol | 5.0 | 5.0 | 3.0 | 3.0 |
| (6) | Hydroxyethyl cellulose | — | — | 0.2 | 0.1 |
| (7) | Purified water | balance | balance | balance | balance |
| | Ratio (A) / (C) (by weight) | 9 | 18 | 3.3 | 2.7 |
| Effects: | | | | | |
| Less sticky feel | | A | A | A | A |
| Less dry/loose feel | | B | B | B | B |
| Smoothness | | A | A | A | A |
| Elasticity | | A | A | A | B |

Notes:
*1: SM8702C, tradename, manufactured by Toray Dow Corning Silicone Co.
*2: SH3775C, tradename, manufactured by Toray Dow Corning Silicone Co.

TABLE 4

| | | Comparative Example | |
|---|---|---|---|
| | | 4 | 5 |
| (1) | Stearyltrimethylammonium chloride | 1.2 | 0.8 |
| | Behenyltrimethylammonium chloride | — | — |
| | 2-Hexyldodecyltrimethylammonium chloride | 0.6 | — |
| | Di-2-hexyldecyldimethylammonium chloride | — | 0.2 |
| (2) | Cetostearyl alcohol | 6.0 | 3.0 |
| (3) | Alkyl saccharide | | |
| | $C_{10}$-O-$(G)_{1.5}$ | — | — |
| | $C_{12}$-O-$(G)_{2.0}$ | — | — |
| | $C_{12}$-O-$(EO)_2$-G | — | — |
| (4) | Dimethylpolysiloxane (1,000 cs) | — | — |
| | Dimethylpolysiloxane (20,000,000 cs) | — | — |
| | Amino-modified silicone*1 | — | — |
| | Polyether-modified silicone*2 | — | — |
| (5) | Propylene glycol | 5.0 | 3.0 |
| (6) | Hydroxyethyl cellulose | — | 0.1 |
| (7) | Purified water | balance | balance |
| | Ratio (A) / (C) (by weight) | — | — |
| Effects: | | | |
| Less sticky feel | | C | D |
| Less dry feel | | C | C |
| Smoothness | | D | C |
| Elasticity | | D | D |

Notes:
*1: SM8702C, tradename, manufactured by Toray Dow Corning Silicone Co.
*2: SH3775C, tradename, manufactured by Toray Dow Corning Silicone Co.

EXAMPLE 8

(Hair Treatment)

Composition:

| | Component | Amount (% by weight) |
|---|---|---|
| (1) | Cetostearyltrimethylammonium chloride | 0.8 |
| (2) | Dicetostearyldimethylammonium chloride | 1.2 |
| (3) | Cetanol | 5.0 |
| (4) | Alkyl saccharide ($C_{12}$-O-$(G)_{1.7}$) | 0.5 |
| (5) | Squalane | 1.0 |
| (6) | Glycerol | 6.0 |
| (7) | Dimethylpolysiloxane (1,000 cs) | 0.5 |
| (8) | Preservative | Appropriate Amount |
| (9) | Colorant | Appropriate Amount |
| (10) | Perfume | Appropriate Amount |
| (11) | Purified water | Balance |
| | Ratio (A) / (C) (by weight): 4 | |

Production method:

To a mixture of the components (8), (9) and (11) heated to 70° C., a mixture of the components (1) to (6), which had been molten by heating to the same temperature, was added. After emulsifying by stirring, the obtained emulsion was cooled to 45° C. under stirring. Then the components (7) and (10) were added thereto and the mixture was further cooled to room temperature under stirring to thereby give the desired composition.

The hair treatment thus obtained gave a good smoothness and a good elasticity to the hair without showing any sticky feel or dry/loose feel at the finishing.

EXAMPLE 9

(Hair Rinse)

Composition:

| | Component | Amount (% by weight) |
|---|---|---|
| (1) | Stearyltrimethylammonium chloride | 0.8 |
| (2) | Dialkyldimethylammonium chloride*[1] | 0.2 |
| (3) | Palmitic acid monoglyceride | 0.5 |
| (4) | Stearyl alcohol | 2.5 |
| (5) | Alkyl saccharide ($C_8$-O-$(G)_{1.4}$) | 0.1 |
| (6) | Liquid paraffin | 0.3 |
| (7) | Dipropylene glycol | 3.0 |
| (8) | Preservative | Appropriate Amount |
| (9) | Colorant | Appropriate Amount |
| (10) | Perfume | Appropriate Amount |
| (11) | Purified water | Balance |
| | Ratio (A) / (C) (by weight): 10 | |

Note; *1: Branched quaternary ammnonium salt derived from a marketed oxo-process alcohol (equivalent volume mixture of Dobanol 23 and Dobanol 45, manufactured by Mitsubishi Petrochemical Co., Ltd.) having 12 to 15 carbon atoms, of a branching ratio of 20%

Production method:

To a mixture of the components (8), (9) and (11) heated to 70° C., a mixture of the components (1) to (7), which had been molten by heating to the same temperature, was added. After emulsifying by stirring, the obtained emulsion was cooled to 45° C. under stirring. Then the component (10) was added thereto and the mixture was further cooled to room temperature under stirring to thereby give the desired composition.

The hair rinse thus obtained gave a good smoothness and a good elasticity to the hair without showing any sticky feel or dry/loose feel at the finishing.

EXAMPLE 10

(Hair Treatment)

Composition:

| | Component | Amount (% by weight) |
|---|---|---|
| (1) | Stearyltrimethylammonium chloride | 3.0 |
| (2) | Myristyl alcohol | 5.0 |
| (3) | Oleic acid monoglyceride | 2.0 |
| (4) | Alkyl saccharide ($C_{12}$-O-$(G)_{2.0}$) | 0.2 |
| (5) | Isostearic acid | 0.5 |
| (6) | Glycine betaine | 0.5 |
| (7) | Diethylene glycol monoethyl ether | 10.0 |
| (8) | Preservative | Appropriate Amount |
| (9) | Colorant | Appropriate Amount |
| (10) | Perfume | Appropriate Amount |
| (11) | Purified water | Balance |
| | Ratio (A) / (C) (by weight): 15 | |

Production method:

To a mixture of the components (8), (9) and (11) heated to 70° C., a mixture of the components (1) to (7), which had been molten by heating to the same temperature, was added. After emulsifying by stirring, the obtained emulsion was cooled to 45° C. under stirring. Then the component (10) was added thereto and the mixture was further cooled to room temperature under stirring to thereby give the desired composition.

The hair treatment thus obtained gave a good smoothness and a good elasticity to the hair without showing any sticky feel or dry/loose feel at the finishing.

EXAMPLE 11

(Hair Conditioner)

Composition:

| | Component | Amount (% by weight) |
|---|---|---|
| (1) | Cetostearyldimethylammonium chloride | 2.5 |
| (2) | Cetostearyl alcohol | 3.0 |
| (3) | Alkyl saccharide ($C_{12}$-O-$(G)_{1.7}$) | 0.2 |
| (4) | Squalane | 1.0 |
| (5) | Propylene glycol | 5.0 |
| (6) | Preservative | Appropriate Amount |
| (7) | Colorant | Appropriate Amount |
| (8) | Perfume | Appropriate Amount |
| (9) | Purified water | Balance |
| | Ratio (A) / (C) (by weight): 12.5 | |

Production method:

To a mixture of the components (6), (7) and (9) heated to 70° C., a mixture of the components (1) to (5), which had been molten by heating to the same temperature, was added. After emulsifying by stirring, the obtained emulsion was cooled to 45° C. under stirring. Then the component (8) was added thereto and the mixture was further cooled to room temperature under stirring to thereby give the desired composition.

The hair conditioner thus obtained gave a good smoothness and a good elasticity to the hair without showing any sticky feel or dry/loose feel at the finishing.

EXAMPLE 12

(Hair Conditioner)

Composition:

| | Component | Amount (% by weight) |
|---|---|---|
| (1) | Cetostearyltrimethylammonium chloride | 0.7 |
| (2) | 2-Dodecylhexadecyltrimethylammonium chloride | 0.4 |
| (3) | Cetanol | 3.0 |
| (4) | Alkyl saccharide ($C_8$-O-(G)$_{1.4}$) | 1.1 |
| (5) | Liquid paraffin | 0.5 |
| (8) | Dimethylpolysiloxane (500 cs) | 0.2 |
| (7) | 2-Octyl dodecanol | 0.5 |
| (8) | Propylene glycol | 5.0 |
| (9) | Hydroxyethyl cellulose | 0.1 |
| (10) | Preservative | Appropriate Amount |
| (11) | Colorant | Appropriate Amount |
| (12) | Perfume | Appropriate Amount |
| (13) | Purified water | Balance |
| | Ratio (A) / (C) (by weight): 1 | |

Production method:

To a mixture of the components (9), (10), (11) and (13) heated to 70° C., a mixture of the components (1) to (8), which had been molten by heating to the same temperature, was added. After emulsifying by stirring, the obtained emulsion was cooled to 45° C. under stirring. Then the component (12) was added thereto and the mixture was further cooled to room temperature under stirring to thereby give the desired composition.

The hair conditioner thus obtained gave a good smoothness and a good elasticity to the hair without showing any sticky feel or dry/loose feel at the finishing.

EXAMPLES 13 AND 14 AND COMPARATIVE EXAMPLES 6 AND 7

Hair rinses of the compositions as listed in Table 5 were produced by the following method and the performance of each product was evaluated by an organoleptic test as specified below. Table 5 summarizes the results.
Organoleptic evaluation method:

20 g of fine hairs (average diameter: 60 μm; length: 15 cm) of a Japanese female subject, which had never been cold-permed nor bleached, was bundled. In the case of a hair cosmetic to be washed away, 2 g of the hair cosmetic was uniformly applied to the hair bundle and then washed away with running water for 30 seconds. After towel-drying, the hair was dried with a dryer. In the case of a hair cosmetic not to be washed away, on the other hand, a definite amount of the hair cosmetic was applied to the hair bundle, followed by air-drying. Then the less sticky feel, less dry/loose feel, smoothness and elasticity of each hair bundle were organoleptically evaluated. A means "very good", B means "good", C means "moderate" and D means "poor".
Production Method:

To the component (9) heated to 70° C., a mixture of the components (1) to (8), which had been molten by heating to the same temperature, was added. After emulsifying by stirring, the emulsion was cooled to room temperature under stirring to thereby give a hair rinse product.

TABLE 5

| | | Example 13 | Example 14 | Comparative Example 6 | Comparative Example 7 |
|---|---|---|---|---|---|
| (1) | Stearyltrimethylammonium chloride | 1.0 | 0.7 | 1.0 | 0.7 |
| (2) | Distearyldimethylammonium chloride | — | 0.5 | — | 0.5 |
| (3) | Stearyl alcohol | 4.0 | 3.0 | 4.0 | 3.0 |
| (4) | Alkyl saccharide ($C_{12}$-O-(G)$_{2.0}$) | 0.4 | 0.2 | — | 0.2 |
| (5) | 50% aqueous suspension of zinc pyrithione*[1] | 0.3 | 0.5 | 0.3 | — |
| (6) | Liquid paraffin | — | 0.5 | — | 0.5 |
| (7) | Propylene glycol | 3.0 | 3.0 | 3.0 | 3.0 |
| (8) | Hydroxyethyl cellulose | 0.5 | 0.5 | 0.5 | 0.5 |
| (9) | Water | balance | balance | balance | balance |
| | Ratio (A) / (C) (by weight) | 2.5 | 6.0 | — | 6.0 |
| | Ratio (A) / (D) (by weight) | 3.3 | 2.4 | 3.3 | — |
| | Effect: | | | | |
| | Less sticky feel | A | B | C | B |
| | Less dry/loose feel | B | A | B | B |
| | Smoothness | B | B | D | C |
| | Elasticity | A | A | C | C |
| | Oil-free fee | A | B | D | D |

Note; *[1]: Tomicide Z-50 (tradename, manufactured by Yoshitomi Pharmaceutical Industries, Ltd.; average particle size: 1 μm)

EXAMPLE 15 AND COMPARATIVE EXAMPLE 8

Hair conditioner products of the following compositions were produced by the methods as specified below.

The performances of these products were evaluated by a pair comparison test with the use of 15 female panelists. In this test, +2 means "very good", +1 means "good" and 0 means "equivocal" and the results are expressed in the number of panelists. Table 2 summarizes the results.

Composition of Hair Conditioner of Example 15

| | Component | Amount (% by weight) |
|---|---|---|
| (1) | Stearyltrimethylammonium chloride | 1.0 |
| (2) | Dicetyldimethylammonium chloride | 0.5 |
| (3) | Cetanol | 4.0 |
| (4) | Alkyl saccharide ($C_{12}$-O-(G)$_{1.7}$) | 0.5 |
| (5) | 50% Aqueous suspension of zinc pyrithione*[1] | 0.6 |
| (6) | Hydroxyethyl cellulose | 0.3 |
| (7) | Propylene glycol | 5.0 |
| (8) | Perfume | 0.4 |
| (9) | Water | balance |
| | Ratio (A) / (C) (by weight): 3.0 | |
| | Ratio (A) / (D) (by weight): 5.0 | |

*[1]: Tomicide Z-50 (tradename, manufactured by Yoshitomi Pharmaceutical Industries, Ltd.; average particle size: 1 μm)

Production method:

To the component (9) heated to 70° C., a mixture of the components (1) to (7), which had been molten by heating to the same temperature, was added. After emulsifying by stirring, the obtained emulsion was cooled to 40° C. under stirring. Then the component (8) was added thereto and the mixture was further cooled to room temperature under stirring to thereby give a hair conditioner product.

Composition of Hair Conditioner of Comparative Example 8

| | Component | Amount (% by weight) |
|---|---|---|
| (1) | Stearyltrimethylammonium chloride | 1.0 |
| (2) | Dicetyldimethylammonium chloride | 0.5 |
| (3) | Cetanol | 4.0 |
| (4) | Hydroxyethyl cellulose | 0.3 |
| (5) | Propylene glycol | 5.0 |
| (6) | Perfume | 0.4 |
| (7) | Water | balance |

Production method:

To the component (7) heated to 70° C., a mixture of the components (1) to (5), which had been molten by heating to the same temperature, was added. After emulsifying by stirring, the obtained emulsion was cooled to 40° C. under stirring. Then the component (6) was added thereto and the mixture was further cooled to room temperature under stirring to thereby give a hair conditioner product.

TABLE 6

| | Example 15 | | | Comparative Example 8 | |
|---|---|---|---|---|---|
| | +2 | +1 | 0 | +1 | +2 |
| Total evaluation | 1 | 4 | 7 | 3 | 0 |
| Less sticky finishing | 2 | 5 | 6 | 2 | 0 |
| Less dry/loose finishing | 0 | 3 | 10 | 2 | 0 |
| Smooth finishing | 1 | 5 | 5 | 3 | 1 |
| Elastic finishing | 2 | 4 | 7 | 2 | 0 |
| Oil-free feel | 2 | 4 | 7 | 2 | 0 |

EXAMPLES 16 TO 19

Hair cosmetics of the compositions specified in Tables 7 and 8 were produced by the following method and the rinse performances of these products were evaluated in accordance with the evaluation method employed in the above Examples 13 and 14. Tables 7 and 8 show the results.

Production method:

To a mixture of the components (7) and (8) heated to 70° C., a mixture of the components (1) to (6), which had been molten by heating to the same temperature, was added. After emulsifying by stirring, the obtained emulsion was cooled to room temperature under stirring.

TABLE 7

| | | Example | | | |
|---|---|---|---|---|---|
| | | 16 | 17 | 18 | 19 |
| (1) | Stearyltrimethyl-ammonium chloride | 1.2 | — | 0.8 | 0.4 |
| | Behenyltrimethyl-ammonium chloride | — | 1.0 | — | 0.2 |
| | 2-Hexyldodecyltri-methylammonium chloride | 0.6 | — | — | 0.2 |
| | Di-2-hexyldecyldi-methylammonium chloride | — | 0.8 | 0.2 | — |
| (2) | Stearyl alcohol | 6.0 | 6.0 | 3.0 | 2.5 |
| (3) | Alkyl saccharide | | | | |
| | $C_{10}$-O-$(G)_{1.5}$ | 0.2 | — | — | — |
| | $C_{12}$-O-$(G)_{2.0}$ | — | 0.1 | — | 0.3 |

TABLE 7-continued

| | | Example | | | |
|---|---|---|---|---|---|
| | | 16 | 17 | 18 | 19 |
| | $C_{12}$-$(EO)_2$-G | — | — | 0.3 | — |
| (4) | Zinc pyrithione*[1] | — | — | 0.3 | 0.2 |
| | Silicone resin*[2] | 0.2 | 0.3 | — | — |
| (5) | Dimethylpolysiloxane (1,000 cs) | 1.0 | — | — | — |
| | Dimethylpolysiloxane (20,000,000 cs) | — | — | 0.2 | — |
| | Amino-modified silicone*[3] | — | 1.0 | — | — |
| | Polyether-modified silicone*[4] | — | — | — | 0.5 |
| | Cyclic silicone (pentamer) | — | — | 2.0 | — |
| 6) | Propylene glycol | 5.0 | 5.0 | 3.0 | 3.0 |
| 7) | Hydroxyethyl cellulose | — | — | 0.3 | 0.3 |
| 8) | Purified water | balance | balance | balance | balance |
| | Ratio (A) / (C) (by weight) | 10 | 18 | 3.3 | 2.7 |
| | Ratio (A) / (D) (by weight) | 9 | 6 | 3.3 | 4 |
| | Effects: | | | | |
| | Less sticky feel | A | A | A | A |
| | Less dry/loose feel | B | B | B | B |
| | Smoothness | A | A | A | A |
| | Elasticity | A | A | A | B |
| | Oil-free feel | A | A | A | A |

TABLE 8

| | | Comparative Example | |
|---|---|---|---|
| | | 9 | 10 |
| (1) | Stearyltrimethyl-ammonium chloride | 1.2 | 0.8 |
| | Behenyltrimethyl-ammonium chloride | — | — |
| | 2-Hexyldodecyltri-methylammonium chloride | 0.6 | — |
| | Di-2-hexyldecyldi-methylammonium chloride | — | 0.2 |
| (2) | Stearyl alcohol | 6.0 | 3.0 |
| (3) | Alkyl saccharide | | |
| | $C_{10}$-O-$(G)_{1.5}$ | — | — |
| | $C_{12}$-O-$(G)_{2.0}$ | — | — |
| | $C_{12}$-$(EO)_2$-G | — | — |
| (4) | Zinc pyrithione*[1] | — | — |
| | Silicone resin*[2] | — | — |
| (5) | Dimethylpolysiloxane (1,000 cs) | — | — |
| | Dimethylpolysiloxane (20,000,000 cs) | — | — |
| | Amino-modified silicone*[3] | — | — |
| | Polyether-modified silicone*[4] | — | — |
| | Cyclic silicone (pentamer) | — | — |
| (6) | Propylene glycol | 5.0 | 3.0 |
| (7) | Hydroxyethyl cellulose | — | 0.1 |
| (8) | Purified water | balance | balance |
| | Ratio (A) / (C) (by weight) | — | — |
| | Ratio (A) / (D) (by weight) | — | — |
| | Effects: | | |
| | Less sticky feel | C | D |
| | Less dry/loose feel | C | C |
| | Smoothness | D | C |

TABLE 8-continued

|  | Comparative Example | |
| --- | --- | --- |
|  | 9 | 10 |
| Elasticity | D | D |
| Oil-free feel | D | D |

Notes;
*1: Zinc pyrithione fine particles described in Example 1 in JP-A-60-16972.
*2: Tospearl 105, tradename, manufactured by Toshiba Silicone Co., (average particle size: 0.5 μm).
*3: SM8702C, tradename, manufactured by Toray Dow Corning Silicone, Co.
*4: SH3775C, tradename, manufactured by Toray Dow Corning Silicone, Co.

EXAMPLE 20

(Hair Treatment)

Composition:

| | Component | Amount (% by weight) |
| --- | --- | --- |
| (1) | Stearyltrimethylammonium chloride | 0.8 |
| (2) | Distearyldimethylammonium chloride | 1.2 |
| (3) | Cetanol | 5.0 |
| (4) | Alkyl saccharide ($C_{12}$-O-(G)$_{1.7}$) | 0.5 |
| (5) | 50% Aqueous suspension of zinc pyrithione*1 | 0.6 |
| (6) | Isopropyl palmitate | 1.0 |
| (7) | Glycerol | 6.0 |
| (8) | Dimethylpolysiloxane (1,000 cs) | 0.5 |
| (9) | Preservative | Appropriate Amount |
| (10) | Colorant | Appropriate Amount |
| (11) | Perfume | Appropriate Amount |
| (12) | Purified water | Balance |
| Ratio (A) / (C) (by weight): 4.0 | | |
| Ratio (A) / (D) (by weight): 6.7 | | |

Note: *1: Tomicide Z-50 (tradename, manufactured by Yoshitomi Pharmaceutical Industries, Ltd.; average particle size: 1 μm)

Production method:

To a mixture of the components (9), (10) and (12) heated to 70° C., a mixture of the components (1) to (7), which had been molten by heating to the same temperature, was added. After emulsifying by stirring, the obtained emulsion was cooled to 45° C. under stirring. Then the components (8) and (11) were added thereto and the mixture was further cooled to room temperature under stirring to thereby give the desired composition.

The hair treatment thus obtained gave a good smoothness, a good elasticity and an oil-free feel to the hair without showing any sticky feel or dry/loose feel at the finishing.

EXAMPLE 21

(Hair Rinse)

Composition:

| | Component | Amount (% by weight) |
| --- | --- | --- |
| (1) | Stearyltrimethylammonium chloride | 0.8 |
| (2) | Dicetyldimethylammonium chloride*1 | 0.2 |
| (3) | Palmitic acid monoglyceride | 0.5 |
| (4) | Stearyl alcohol | 2.5 |
| (5) | Alkyl saccharide ($C_8$-O-(G)$_{1.4}$) | 0.1 |
| (6) | Silicone resin*2 | 0.3 |
| (7) | Liquid paraffin | 0.3 |
| (8) | Dipropylene glycol | 3.0 |
| (9) | Preservative | Appropriate Amount |
| (10) | Colorant | Appropriate Amount |
| (11) | Perfume | Appropriate Amount |
| (12) | Purified water | Balance |
| Ratio (A) / (C) (by weight): 10.0 | | |
| Ratio (A) / (D) (by weight): 5.0 | | |

Notes;
*1: Branched quaternary ammonium salt derived from a marketed oxo-process alcohol (equivalent volume mixture of Dobanol 23 and Dobanol 45, manufactured by Mitsubishi Petrochemical Co., Ltd.) of a branching ratio of 20%
*2: Tospearl 105 (tradename, manufactured by Toshiba Silicone Co.; average particle size: 0.5 μm)

Production method:

To a mixture of the components (9), (10) and (12) heated to 70° C., a mixture of the components (1) to (8), which had been molten by heating to the same temperature, was added. After emulsifying by stirring, the obtained emulsion was cooled to 45° C. under stirring. Then the component (11) was added thereto and the mixture was further cooled to room temperature under stirring to thereby give the desired composition.

The hair rinse thus obtained gave a good smoothness, a good elasticity and an oil-free feel to the hair without showing any sticky feel or dry/loose feel at the finishing.

EXAMPLE 22

(Hair Treatment)

Composition:

| | Component | Amount (% by weight) |
| --- | --- | --- |
| (1) | Stearyltrimethylammonium chloride | 3.0 |
| (2) | Behenyl alcohol | 3.0 |
| (3) | Stearyl alcohol | 2.0 |
| (4) | Oleic acid monoglyceride | 2.0 |
| (5) | Alkyl saccharide ($C_{12}$-O-(G)$_{2.0}$) | 0.2 |
| (6) | Mica particles*1 | 0.2 |
| (7) | Isostearic acid | 0.5 |
| (8) | Cholesterol isostearate | 0.3 |
| (9) | Diethylene glycol monoethyl ether | 10.0 |
| (10) | Preservative | Appropriate Amount |
| (11) | Colorant | Appropriate Amount |
| (12) | Perfume | Appropriate Amount |
| (13) | Purified water | Balance |
| Ratio (A) / (C) (by weight): 15.0 | | |
| Ratio (A) / (D) (by weight): 15.0 | | |

Note: *1: KS-220 (tradename, manufactured by Yamaguchi Unmo Kogyosho K.K.; average particle size: 3 μm)

Production method:

To a mixture of the components (10), (11) and (13) heated to 70° C., a mixture of the components (1) to (9) which, had been molten by heating to the same temperature, was added. After emulsifying by stirring, the obtained emulsion was cooled to 45° C. under stirring. Then the component (12) was added thereto and the mixture was further cooled to room temperature under stirring to thereby give the desired composition.

23

The hair treatment thus obtained gave a good smoothness, a good elasticity and an oil-free feel to the hair without showing any sticky feel or dry/loose feel at the finishing.

EXAMPLE 23

(Hair Conditioner)

Composition:

| | Component | Amount (% by weight) |
|---|---|---|
| (1) | Stearyldimethylammonium chloride | 2.5 |
| (2) | Stearyl alcohol | 3.0 |
| (3) | Alkyl saccharide ($C_{12}$-O-(G)$_{1.7}$) | 0.2 |
| (4) | Poly(methyl methacrylate)*[1] | 0.2 |
| (5) | Squalane | 1.0 |
| (6) | Propylene glycol | 5.0 |
| (7) | Preservative | Appropriate Amount |
| (8) | Colorant | Appropriate Amount |
| (9) | Perfume | Appropriate Amount |
| (10) | Purified water | Balance |
| Ratio (A) / (C) (by weight): 12.5 | | |
| Ratio (A) / (D) (by weight): 12.5 | | |

Note: *1: Microsphere M-10 (tradename, manufactured by Matsumoto Yushi Seiyaku K.K.; average particle size: 8 μm)

Production method:

To a mixture of the components (7), (8) and (10) heated to 70° C., a mixture of the components (1) to (6), which had been molten by heating to the same temperature, was added. After emulsifying by stirring, the obtained emulsion was cooled to 45° C. under stirring. Then the component (9) was added thereto and the mixture was further cooled to room temperature under stirring to thereby give the desired composition.

The hair conditioner thus obtained gave a good smoothness, a good elasticity and an oil-free feel to the hair without showing any sticky feel or dry/loose feel at the finishing.

EXAMPLE 24

(Hair Conditioner)

Composition:

| Component | Amount (% by weight) |
|---|---|
| (1) Stearyltrimethylammonium chloride | 0.7 |
| (2) 2-Dodecylhexadecyltrimethylammonium chloride | 0.4 |
| (3) Cetanol | 3.0 |
| (4) Alkyl saccharide ($C_8$-O-(G)$_{1.4}$) | 1.1 |
| (5) Crosslinked polystyrene*[1] | 0.4 |
| (6) Liquid paraffin | 0.5 |
| (7) Dimethylpolysiloxane (500 cs) | 0.2 |
| (8) 2-Octyl dodecanol | 0.5 |
| (9) Propylene glycol | 5.0 |
| (10) Hydroxyethyl cellulose | 0.1 |
| (11) Preservative | Appropriate Amount |
| (12) Colorant | Appropriate Amount |
| (13) Perfume | Appropriate Amount |
| (14) Purified water | Balance |

Note; *1: Finepearl PB-300 (tradename, manufactured by Sumitomo Chemical Co., Ltd.; average particle size: 15 μm)
Ratio (A)/(C)(by weight): 1.0
Ratio (A)/(D)(by weight): 2.8

Production method:

To a mixture of the components (10), (11), (12) and (14) heated to 70° C., a mixture of the components (1) to (9), which had been molten by heating to the same temperature, was added. After emulsifying by stirring, the obtained emulsion was cooled to 45° C. under stirring. Then the component (13) was added thereto and the mixture was further cooled to room temperature under stirring to thereby give the desired composition.

The hair conditioner thus obtained gave a good smoothness, a good elasticity and an oil-free feel to the hair without showing any sticky feel or dry/loose feel at the finishing.

While the invention has been described in detail and with reference to specific examples thereof, it will be apparent to one skilled in the art that various changes and modifications can be made therein without departing from the spirit and scope thereof.

What is claimed is:

1. A hair cosmetic, consisting essentially of the following components (A), (B), and (C):

(A) 0.1 to 20% by weight, based on the total weight of said composition, of a quaternary ammonium salt having the formula (2) or (3):

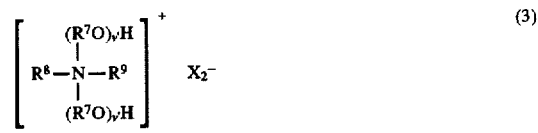

wherein at least one of $R^3$, $R^4$, $R^5$ and $R^6$ represents an alkyl or alkenyl group having 8 to 28 carbon atoms in total and which is unsubstituted or substituted by an alkoxyl, alkenyloxy, alkanoylamino or alkenoylamino group, and the others each represent a benzyl group or an alkyl or hydroxyalkyl group having 1 to 5 carbon atoms;

$R^7$ represents an alkylene group having 2 or 3 carbon atoms;

$X_1^-$ and $X_2^-$ each represents a halogen ion or an organic ion;

v and v' each represents an integer of from 1 to 20; and at least one of $R^8$ and $R^9$ represents an alkyl or alkenyl group having 8 to 28 carbon atoms in total and which is unsubstituted or substituted by an alkoxyl, alkenyloxy, alkanoylamino or alkenoylamino group, and each of the others represents a benzyl group or an alkyl or hydroxyalkyl group having 1 to 5 carbon atoms;

(B) 0.5 to 20% by weight, based on the total weight of said composition, of a fat or oil or both in combination, selected from the group consisting of fatty alcohols, hydrocarbon oils, lanolin, lanolin fatty acids, fatty acid esters, fatty acids, alkyl or alkenylamide amines and mixtures thereof; and (C) an alkyl saccharide surfactant represented by the following formula (1):

$$R^1—O—(R^2O)_m—G_n \tag{1}$$

wherein

R$^1$ represents a straight chain or branched chain alkyl, alkenyl or alkylphenyl group having 8 to 18 carbon atoms;

R$^2$ represents an alkylene group having 2 to 4 carbon atoms;

m represents a number of 0 to 4;

G represents a reducing sugar having 5 or 6 carbon atoms; and n represents a number of 1 to 10;

wherein the weight ratio of component (A) to (C) is from 1 to 20.

2. The hair cosmetic of claim 1, which further comprises the following component (D):

(D) fine particles of an average particle size of 100 μm or below, wherein the weight ratio of component (A) to component (D) is from 1 to 20.

3. The hair cosmetic of claim 1, wherein said quaternary ammonium salt is selected from the group consisting of dialkyldimethylammonium chlorides having an alkyl group of 8 to 16 carbon atoms and having a branching ration of 10 to 50% by mol.

4. The hair cosmetic of claim 1, wherein said quaternary ammonium salt is selected from the group consisting of 2-decyltetradecyltrimethylammonium chloride, 2-dodecylhexadecyltrimethylammonium chloride, di-2-hexyldecyldimethylammonium chloride and di-2-octyldodecyldimethylammonium chloride.

5. The hair cosmetic of claim 1, wherein said quaternary ammonium salt has the formula:

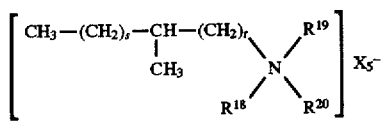

wherein R$^{18}$ represents a group of the formula:

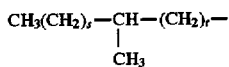

wherein s represents an integer of from 2 to 14, and t represents an integer of from 3 to 11, and wherein the sum of s and t is 15; or an alkyl group of 1 to 3 carbon atoms; and R$^{19}$ and R$^{20}$ each represents a benzyl group or an alkyl or hydroxyalkyl group having 1 to 3 carbon atoms; and X$_5^-$ represents a halogen ion or an organic ion.

6. The hair cosmetic of claim 1, wherein said fat or oil is selected from the group consisting of monoglycerides of saturated and unsaturated, straight-chain or branched fatty acids having 12 to 24 carbon atoms, higher alcohols having straight-chain and branched alkyl and alkenyl group(s) having 12 to 26 carbon atoms.

7. The hair cosmetic of claim 1, wherein for said alkyl saccharide surfactant, R$^1$ represents an alkyl group having 8 to 12 carbon atoms; and G is selected from the group consisting of glucose, galactose and fructose.

8. The hair cosmetic of claim 2, wherein said particles of (D) are made of material selected from the group consisting of nylon, polyethylene, polyester, polypropylene, polystyrene, polyurethane, polyamide, epoxy resins, urea resins, acryl polymers, silicone resins, talc, kaolin, mica, bentonite, sericite, selenium desulfide and zinc pyrithione.

9. The hair cosmetic of claim 1, which further comprises the following component (E):

(E) 0.05 to 20% by weight, based on the total weight of said composition, of a silicone compound selected from the group consisting of:

(a) compounds of the following formula (7):

$$(CH_3)_3SiO[(CH_3)_2SiO]_{n1}Si(CH_3)_3 \tag{7}$$

wherein n1 is an integer of 3 to 9,000;

(b) compounds of the following formula (8):

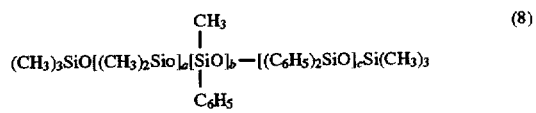

wherein a, b and c are numbers the sum of which exceeds 1, provided that c is not 0 when b is 0 and b is not 0 when c is 0, and further provided that the sum of a, b and c is 20,000 or less; (c) compounds of the following formula (9):

$$(R'_dA_{(3-d)})—Si—(OSi(A)_2)_{n2}—[OSi(A_eR'_{(2-e)})]_{n3}—OSi(R'_dA_{(3-d)}) \tag{9}$$

wherein

A represents a hydrogen atom or a group selected from the group consisting of a phenyl group, a hydroxyl group and an alkyl group having 1 to 8 carbon atoms;

d is an integer of from 0 to 3;

e is 0 or 1;

n2 is an integer of from 0 to 1,999;

n3 is an integer of from 1 to 2,000, provided that the sum of n2 and n3 is an integer of from 1 to 2,000; and R' is a group —C$_f$H$_{2f}$L, wherein f is an integer of from 2 to 8; and L is selected from the group consisting of:

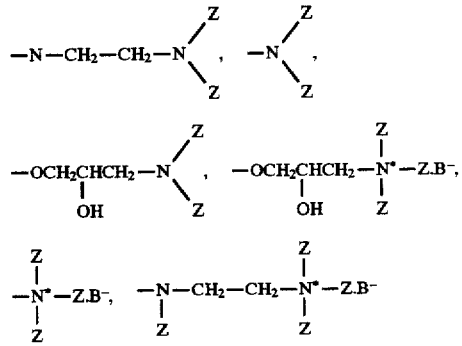

wherein Z represents a hydrogen atom or a group selected from the group consisting of a phenyl group, a benzyl group and an alkyl group having 1 to 20 carbon atoms; and $B^-$ represents $Cl^-$, $Br^-$, $I^-$ or $F^-$;

(d) compounds of the following formula (10):

$$(CH_3)_3SiO[SiO]_g[SiO]_h\text{———}[SiO]_i-Si(CH_3)_3 \quad (10)$$

with side groups: $CH_3$, $CH_3$, $CH_3$ $(CH_2)_j OCOR^{22}$, $(CH_2)_j OCOR^{22}$, $(CH_2)_j OCOR^{22}$ wherein g, h and i are each a number of from 1 to 350;
j is a number of from 0 to 10; and
$R^{22}$ represents an alkyl group having 9 to 21 carbon atoms;

(e) compounds of the following formulae (11-a) or (11-b):

$$HO-(CH_2)-R^{23}-[SiO]_k-Si-R^{23'}-CH_2OH \quad (11\text{-}a)$$

with side groups $CH_3$, $CH_3$, $CH_3$, $CH_3$ wherein k is a number of from 1 to 500; and
$R^{23}$ and $R^{23'}$ represent each a single bond or an alkylene group having 1 to 4 carbon atoms;

(f) compounds of the following formula (12):

$$(CH_3)_3SiO-[SiO]_{m1}[SiO]_o\text{———}[SiO]_{q1}-Si(CH_3)_3 \quad (12)$$

with side groups: $CH_3$, $CH_3$, $(CH_2)_r OR^{24}$, $CH_3$, $(CH_2)_r OR^{24}$, $(CH_2)_r OR^{24}$ wherein m1, o and q1 are each a number the sum of which is from 1 to 300;
r is a number of from 0 to 5; and
$R^{24}$ represents an alkyl group having 4 to 22 carbon atoms;

(g) compounds of the following formulae (13) to (16):

$$CH_3-Si(CH_3)_2-O-[Si(CH_3)_2-O]_{m2}-[Si(CH_3)_2-O]_{n4}-Si(CH_3)_2-CH_3 \quad (13)$$

$$R^{25}-Si(CH_3)_2-O-[Si(CH_3)_2-O]_{m2}-Si(CH_3)_2-R^{25} \quad (14)$$

$$R^{25}-Si(CH_3)_2-O-[Si(CH_3)_2-O]_{m2}-[Si(CH_3)(R^{25})-O]_{n4}-Si(CH_3)_2-R^{25} \quad (15)$$

$$CH_3-Si(CH_3)_2-O-[[Si(CH_3)_2-O]_{m2}-(CH_2)_{z1}-O-(C_2H_4O)_{x1}-(C_3H_6O)_{y1}-(CH_2)_{z1}]_{n4}-Si(CH_3)_2-CH_3 \quad (16)$$

wherein $R^{25}$ represents a group $-(CH_2)_{z1}-O-(C_2H_4O)_{x1}-(C_3H_6O)_{y1}-A_1$, wherein $A_1$ represents an alkyl group having 1 to 12 carbon atoms or a hydrogen atom; x1 is a number of from 0 to 50; y1 is a number of from 0 to 50, provided that the sum of x1 and y1 is 1 or above; z1 is a number of from 0 to 10; m2 is a number of from 1 to 2,000; and n4 is a number of from 1 to 1,000;

(h) compounds of the following formula (17):

$$(CH_3)_3SiO[SiO]_\alpha[SiO]_\beta-Si(CH_3)_3 \quad (17)$$

with side groups $CH_3$, $CH_3$, $CH_3$, $R^{26}-CH\underset{O}{\overset{}{\diagdown\diagup}}CH_2$ wherein α is a number of from 1 to 500;
β is a number of from 1 to 50; and
$R^{26}$ is an alkylene group having 1 to 3 carbon atoms;

(i) compounds of the following formula (18):

$$(CH_3)_3SiO(SiO)_\gamma-Si(CH_3)_3 \quad (18)$$

with side groups $CH_3$, $(CH_2)_2$, $CF_3$ wherein γ is a number of from 1 to 400;

(j) compounds of the following formula (19):

$$\left[\begin{array}{c} R^{27} \\ | \\ [SiO]_\delta \\ | \\ R^{27} \end{array}\right] \quad (19)$$

wherein

δ is a number of from 3 to 8; and
$R^{27}$ represents an alkyl group having 1 to 3 carbon atoms; and (k) compounds of the following formulae (20-a) or (20-b):

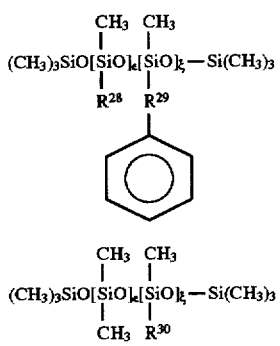

(20-a)

(CH₃)₃SiO[SiO]ₑ[SiO]ζ—Si(CH₃)₃ with R²⁸, R²⁹ substituents (CH₃)₃SiO[SiO]ₑ[SiO]ζ—Si(CH₃)₃ (20-b)

with CH₃, R³⁰ substituents wherein $\epsilon$ and $\zeta$ are each a number of from 1 to 500;

$R^{28}$ represents an alkyl group having 2 to 18 carbon atoms;

$R^{29}$ represents a single bond or an alkylene group having 1 to 4 carbon atoms; and $R^{30}$ represents an alkyl group having 10 to 16 carbon atoms.

10. The hair cosmetic of claim 2, which further comprises the following component (E):

(E) 0.05 to 20% by weight, based on the total weight of said composition, of a silicone compound selected from the group consisting of:

(a) compounds of the following formula (7):

$$(CH_3)_3SiO[(CH_3)_2SiO]_{n1}Si(CH_3)_3 \quad (7)$$

wherein n1 is an integer of 3 to 9,000;

(b) compounds of the following formula (8):

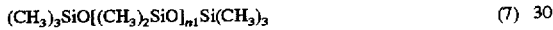

(8)

(CH₃)₃SiO[(CH₃)₂SiO]ₐ[SiO]ᵦ—[(C₆H₅)₂SiO]ᶜSi(CH₃)₃

|
C₆H₅ wherein a, b and c are numbers the sum of which exceeds 1, provided that c is not 0 when b is 0 and b is not 0 when c is 0, and further provided that the sum of a, b and c is 20,000 or less;

(c) compounds of the following formula (9):

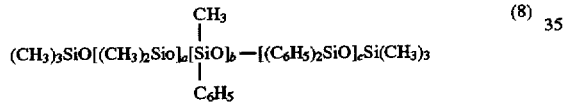

$(R'_dA_{(3-d)})$—Si—$(OSi(A)_2)_{n2}$—$[OSi(A_eR'_{(2-e)})]_{n3}$—$OSi(R'_dA_{(3-d)})$  (9)

wherein

A represents a hydrogen atom or a group selected from the group consisting of a phenyl group, a hydroxyl group and an alkyl group having 1 to 8 carbon atoms;

d is an integer of from 0 to 3;

e is 0 or 1;

n2 is an integer of from 0 to 1,999;

n3 is an integer of from 1 to 2,000, provided that the sum of n2 and n3 is an integer of from 1 to 2,000; and R' is a group —$C_fH_{2f}L$, wherein f is an integer of from 2 to 8; and L is selected from the group consisting of:

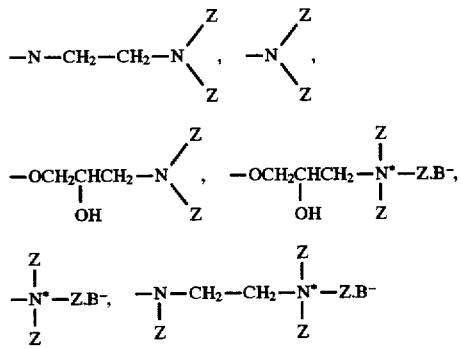

—N(Z)—CH₂—CH₂—N(Z)(Z) , —N(Z)(Z) ,

—OCH₂CH(OH)CH₂—N(Z)(Z) , —OCH₂CH(OH)CH₂—N⁺(Z)(Z)—Z.B⁻ ,

—N⁺(Z)(Z)(Z)—Z.B⁻ , —N(Z)—CH₂—CH₂—N⁺(Z)(Z)—Z.B⁻ wherein Z represents a hydrogen atom or a group selected from among a phenyl group, a benzyl group and an alkyl group having 1 to 20 carbon atoms; and B⁻ represents Cl⁻, Br⁻, I⁻ or F⁻;

(d) compounds of the following formula (10):

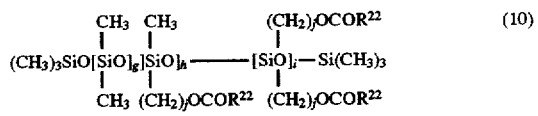

(10)

(CH₃)₃SiO[SiO]_g[SiO]_h—[SiO]_i—Si(CH₃)₃ with CH₃, CH₃, (CH₂)ⱼOCOR²², (CH₂)ⱼOCOR²² substituents wherein g, h and i are each a number of from 1 to 350;

j is a number of from 0 to 10; and $R^{22}$ represents an alkyl group having 9 to 21 carbon atoms;

(e) compounds of the following formulae (11-a) or (11-b):

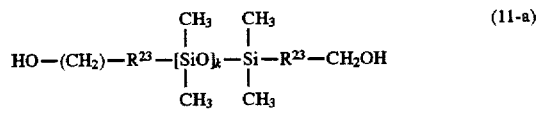

(11-a)

HO—(CH₂)—R²³—[SiO]ₖ—Si—R²³—CH₂OH wherein k is a number of from 1 to 500; and $R^{23}$ and $R^{23'}$ represent each a single bond or an alkylene group having 1 to 4 carbon atoms;

(f) compounds of the following formula (12):

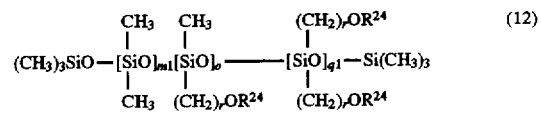

(12)

(CH₃)₃SiO—[SiO]ₘ₁[SiO]ₒ—[SiO]_{q1}—Si(CH₃)₃ with CH₃, (CH₂)ᵣOR²⁴, (CH₂)ᵣOR²⁴ substituents wherein m1, o and q1 are each a number the sum of which is from 1 to 300;

r is a number of from 0 to 5; and $R^{24}$ represents an alkyl group having 4 to 22 carbon atoms;

(g) compounds of the following formulae (13) to (16):

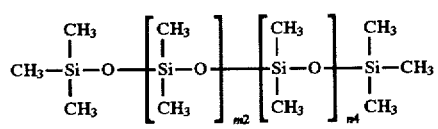

(13)

CH₃—Si(CH₃)₂—O—[Si(CH₃)₂—O]_{m2}—[Si(CH₃)₂—O]_{n4}—Si(CH₃)₂—CH₃

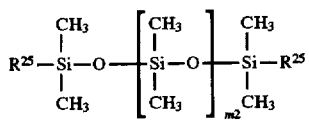
(14)

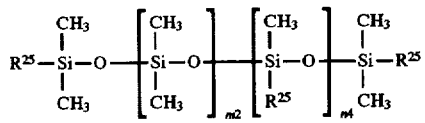
(15)

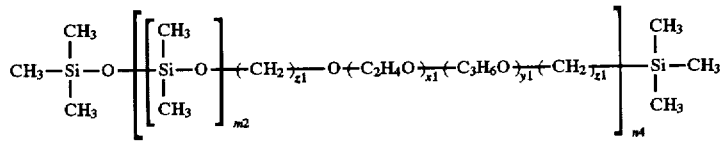
(16)

wherein $R^{25}$ represents a group —$(CH_2)_{z1}$—O—$(C_2H_4O)_{x1}$—$(C_3H_6O)_{y1}$—$A_1$, wherein $A_1$ represents an alkyl group having 1 to 12 carbon atoms or a hydrogen atom; x1 is a number of from 0 to 50; y1 is a number of from 0 to 50, provided that the sum of x1 and y1 is 1 or above; z1 is a number of from 0 to 10; m2 is a number of from 1 to 2,000; and n4 is a number of from 1 to 1,000;

(h) compounds of the following formula (17):

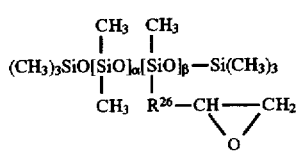
(17)

wherein

α is a number of from 1 to 500;

β is a number of from 1 to 50; and $R^{26}$ is an alkylene group having 1 to 3 carbon atoms;

(i) compounds of the following formula (18):

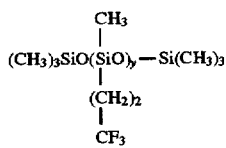
(18)

wherein γ is a number of from 1 to 400;

(j) compounds of the following formula (19):

$$\left[ \begin{array}{c} R^{27} \\ | \\ SiO_{b} \\ | \\ R^{27} \end{array} \right]$$
(19)

wherein

δ is a number of from 3 to 8; and $R^{27}$ represents an alkyl group having 1 to 3 carbon atoms; and (k) compounds of the following formulae (20-a) or (20-b):

$$(CH_3)_3SiO[SiO]_\epsilon[SiO]_\zeta-Si(CH_3)_3$$
with substituents $CH_3, CH_3$ on top and $R^{28}, R^{29}$—phenyl below
(20-a)

$$(CH_3)_3SiO[SiO]_\epsilon[SiO]_\zeta-Si(CH_3)_3$$
with $CH_3, CH_3$ on top and $CH_3, R^{30}$ below
(20-b)

wherein

ε and ζ are each a number of from 1 to 500;

$R^{28}$ represents an alkyl group having 2 to 18 carbon atoms;

$R^{29}$ represents a single bond or an alkylene group having 1 to 4 carbon atoms; and $R^{30}$ represents an alkyl group having 10 to 16 carbon atoms.

* * * * *